United States Patent
Sastry et al.

(10) Patent No.: US 8,274,293 B2
(45) Date of Patent: Sep. 25, 2012

(54) APPARATUS AND METHOD FOR MEASUREMENT OF PH OVER A WIDE RANGE OF PRESSURE

(75) Inventors: Sudhir K. Sastry, Dublin, OH (US); Chaminda P. Samaranayake, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 438 days.

(21) Appl. No.: 12/672,975

(22) PCT Filed: Sep. 10, 2008

(86) PCT No.: PCT/US2008/075826
§ 371 (c)(1),
(2), (4) Date: Feb. 10, 2010

(87) PCT Pub. No.: WO2009/036041
PCT Pub. Date: Mar. 19, 2009

(65) Prior Publication Data
US 2011/0248731 A1  Oct. 13, 2011

Related U.S. Application Data

(60) Provisional application No. 60/971,068, filed on Sep. 10, 2007.

(51) Int. Cl.
*G01N 27/416* (2006.01)
(52) U.S. Cl. ..... 324/438; 324/453; 324/693; 204/228.6; 204/433
(58) Field of Classification Search ............ 324/438, 324/453, 693, 71.1; 204/228.6, 433
See application file for complete search history.

(56) References Cited

U.S. PATENT DOCUMENTS

| | | | |
|---|---|---|---|
| 3,056,094 A | 5/1976 | Capuano | |
| 4,445,091 A | 4/1984 | Kusebauch et al. | |
| 5,110,441 A * | 5/1992 | Kinlen et al. | 204/418 |
| 5,336,388 A | 8/1994 | Leader et al. | |
| 5,489,371 A | 2/1996 | Joseph et al. | |
| 5,497,091 A * | 3/1996 | Bratton et al. | 324/348 |
| 6,503,831 B2 | 1/2003 | Speakman | |
| 6,860,984 B2 | 3/2005 | Bannigan et al. | |

(Continued)

FOREIGN PATENT DOCUMENTS
WO  2006/102905 A1  10/2006

OTHER PUBLICATIONS

Stippl, V.M. et al., Optical Method for the in-situ Measurement of the pH-value During High Pressure Treatment of Foods, High Pressure Research, 2002, pp. 757-761 (22).

(Continued)

*Primary Examiner* — Vincent Q Nguyen
(74) *Attorney, Agent, or Firm* — Standley Law Group LLP

(57) ABSTRACT

A sensor for measuring the pH of a solution of the present invention includes: (a) a tubular body portion constructed from a flexible electrically-insulating material, the tubular body portion having an interior passage; (b) a first reverse osmosis membrane disposed in the interior passage; (c) a second reverse osmosis membrane disposed in the interior passage; (d) a proton conducting membrane disposed between the first reverse osmosis membrane and the second reverse osmosis membrane in the interior passage; (e) a first electrode; and (f) a second electrode.

11 Claims, 2 Drawing Sheets

U.S. PATENT DOCUMENTS

2004/0005474 A1  1/2004  Charnock et al.

OTHER PUBLICATIONS

Crolet, J.L. et al., pH Measurements in Aqueous CO2 Solutions Linder High Pressure and Temperature, Corrosion—NACE, Feb. 1983, pp. 39-46, 39(2).

Crolet, J.L. et al., pH Measurements under high pressures of CO2 and H2S, Materials Performance, May 1984, pp. 35-42.

Crow, D.R., Principles and Applications of Electrochemistry, 1988, pp. 50-53, Chapman and Hall, New York.

Cruanes, M T. et al., Electrochemical Measurements at High Pressure: Solvation and Thermodynamics of Electron-Transfer Reactions, The Journal of Physical Chemistry, 1992, pp. 9888-9892, 96(24).

Distèche, A., pH Measurements with a Glass Electrode Withstanding 1500 kg/cm2 Hydrostatic Pressure, The Review of Scientific Instruments, Jun. 1959. pp. 474-478, 30(6).

Dupont Fuel Cells, DuPont Nafion PFSA Membranes NE-1135, N-115, N-117, NE-1110, 2005, pp. 1-4, Fayetteville, NC.

El'Yanov, B.S., Linear Free Energy Relationship and Some Quantitative Regularities of the Effect of Pressure on Chemical Reactions, Aust. J. Chem. 1975, pp. 933-943, 28.

Hayert, M. et al., A Simple Method for Measuring the pH of Acid Solutions Under High Pressure, J. Phys. Chem. A, 1999, pp. 1785-1789, 103(12).

Hitchens, T.K. et al., Pressure Dependence of Weak Acid Ionization in Deuterium Oxide Solutions, J. Phys. Chem. B, 1998, pp. 1002-1004, 102(6).

Kalinina. A.G. et al., Conductometric Measurements At Pressures From 1 to 7000 kg/cm2, International Corrosion Conference Series, 1976, pp. 158-163.

Kitamura, Y. et al., Reaction Volume of Protonic Ionization for Buffering Agents. Prediction of Pressure Dependence of pH and pOH, Journal of Solution Chemistry, 1987, pp. 715-725, 16(9).

NIST, Isothermal Properties for Water, 2008, pp. 1-3, National Institute of Standards and Technology.

Sastry, S.K., Electrical Conductivity of Foods, Chapter 10 in Engineering Properties of Foods, 2005, pp. 1-73, CRC Press, Boca Raton, Florida.

Stippl, V.M. et al., Ionization equilibria at high pressure, Eur Food Res Technol, 2005, pp. 151-156, 221.

* cited by examiner

APPARATUS AND METHOD FOR MEASUREMENT OF PH OVER A WIDE RANGE OF PRESSURE

CROSS-REFERENCE TO RELATED APPLICATIONS

This application claims the priority benefit of U.S. Patent Application No. 60/971,068, filed Sep. 10, 2007, which is hereby incorporated by reference in its entirety.

TECHNICAL FIELD OF THE INVENTION

The present invention is in the field of pH sensors. Specifically, the present invention relates to pH sensors capable of operation over a wide range of pressures and in electrically "noisy" environments.

BACKGROUND OF THE INVENTION

The measurement of pH (log 1/[hydrogen ion concentration]) of a material is a common and routine analytical activity used in a variety of industries. A commonly used device has a pH electrode and a reference electrode, which, when contacted with the sample, comprise an electrochemical cell. The electromotive force so generated by this cell may be calibrated against the pH of the sample.

The principal limitation of this approach is that these devices are not suited to operation under extreme conditions of pressure (up to and exceeding 1000 MPa). In addition to mechanical strength considerations; the reaction equilibria (as well as the diffusive mass transport necessary for achievement of such equilibria) are altered in complex ways by pressure, resulting in uncertainty regarding changes in sensor response under these extreme conditions. The feed-through wires used in pressurized experimental set-ups are prone to electrical interference, resulting in noisy signals that obscure the millivolt-level readings of such sensors. Experiments with such sensors (iridium-iridium oxide sensing electrode and silver-silver-chloride reference electrode, for example) have suggested that reproducibility is a major issue—sensors typically take up to eight cycles of pressurization before consistent results are obtained. Further, such sensors break down frequently.

Methods described for determination of pH at high pressures typically use data on reaction volumes under atmospheric pressure, and using thermodynamic considerations to calculate pH under pressure. These methods represent calculations that have not been experimentally verified. Still another method measures optical properties of transparent solutions and relates these to pH. However, such a method is not applicable to most real materials, which are opaque.

The pressure affects reaction equilibria and conformation of molecules leading to pH changes under high pressure. The measurement of pH under pressure has been investigated over the past several decades. Disteche (1959) made a glass pH electrode capable to withstand high hydrostatic pressure up to 1500 kg/cm$^2$ (147 MPa). The electrode assembly also consisted of two Ag/AgCl electrodes and was designed to use pH measurements at great ocean depth. Crolet and Bonis (1983 and 1984) also used a glass pH electrode with a Ag/AgCl reference electrode to measure pH under pressure from 0.1 up to 100 MPa. The fragile nature of glass pH electrode however limits its use under high pressures above 150 MPa. In addition, it is reported that the electrode potential of the Ag/AgCl reference electrode is pressure dependent (Cruanes et al., 1992), which makes the pH measurement more complicated under pressure.

High pressure pH measurements (up to 450 MPa) were also performed using optical methods (Hitchens and Bryant, 1998; Hayert et al., 1999; Stippl et al., 2002). These methods involve indicator dyes and are not suitable for opaque samples such as food.

In addition to the above in-situ methods, pH of buffer solutions has been calculated using the electrical conductivities measured under high pressure (Kalinina and Kryukov, 1976). This is however not a direct method of measuring pH and is not applicable for complex samples such as food. The pH of buffer solutions under high pressure was also calculated using the experimental values of reaction volume under atmospheric pressure (El'yanov, 1975; Kitamura and Itoh, 1987). Their theoretical models assume reaction volume is pressure independent, which may not be true in reality.

SUMMARY OF THE INVENTION

The present invention is based on the principle that the electrical conductivity of an electrolytic solution is a function of the mobilities of each of the constituent ions. Normally, the electrical conductivity of such a solution would depend on each of the ionic species present in the solution, and not on the hydrogen ion concentration alone. However, if it were possible to selectively filter the ions such that the only contribution to electrical current was due to the flux of hydrogen ions alone, it would then be possible to relate the electrical conductivity (or resistivity, or, in systems of defined geometry, resistance or current) to pH.

Such filtering is possible, given the widespread availability of various membranes. For example, a class of proton conducting membranes is currently used in hydrogen fuel cells to allow the passage of hydrogen ions; however, they also allow the passage of other cations. For further exclusion of cations, it is possible to use reverse osmosis membranes which are in common use for water purification. By use of the appropriate combination of such membranes, it is possible to achieve the filtering described above. In addition to these requirements, the sensor must be capable of transmitting an external pressure to the sample. In situations when the test sample is different from the surrounding pressurizing medium, the device may be made with flexible walls to permit the environmental pressure to be transmitted to the sample fluid without mixing the two materials. Alternatively, when the pH of an environment is desired (as for example the pH of seawater at great depths, a more open structure may be used to facilitate ingress of the environmental fluid into the sensor.

A sensor for measuring the pH of a solution of the present invention comprises: (a) a body portion constructed from a flexible electrically-insulating material, the body portion having an interior passage; (b) a first reverse osmosis membrane disposed in the interior passage; (c) a second reverse osmosis membrane disposed in the interior passage; (d) a proton conducting membrane disposed between the first reverse osmosis membrane and the second reverse osmosis membrane in the interior passage; (e) a first electrode; and (f) a second electrode.

The sensor is connected to a power supply in electrical communication with the first electrode and the second electrode. Measurement instrumentation involves a voltmeter, or voltage transducer for voltage measurement, and an ammeter or current transducer for measurement of current passing through the sample. The power supply and measurement instrumentation should preferably be located outside the pressurized environment, communicating with the sensor via wires which enter the pressurized environment via leadthroughs. Alternatively, if power supplies and instrumentation are capable of withstanding extremes of pressure, they may be placed within the pressure environment, provided a means exists for recovery and recording of data by humans under ordinary atmospheric conditions.

In some embodiments of the present invention, the proton conducting membrane is a Nafion® membrane (DuPont, 2007).

In some embodiments of the present invention, the flexible electrically-insulating material is a polymerized siloxane.

In some embodiments of the present invention, the flexible electrically-insulating material retains its flexibility in the pressure range of from about 0.1 MPa to about 850 MPa.

In some embodiments of the present invention, the sensor is operational in the pressure range of from about 0.1 MPa to about 850 MPa. In some embodiments of the present invention the sensor is operational at pressures exceeding 1000 MPa.

In some embodiments of the present invention, the first electrode comprises a material preferably having a wide electrochemical window, and is selected from the group consisting of: gold, platinum, titanium, boron-doped diamond, or graphite.

In some embodiments of the present invention, the second electrode comprises the same material as the first electrode.

In some embodiments of the present invention, the first reverse osmosis membrane is a thin film membrane (e.g. GE Sepa™ CF TF (thin film) RO SE membrane).

In some embodiments of the present invention, the second reverse osmosis membrane is the same as the first membrane.

DETAILED DESCRIPTION OF THE PREFERRED EMBODIMENT(S)

In accordance with the foregoing summary, the following presents a detailed description of the preferred embodiments of the invention that is currently considered to be the best mode.

Figure 1:
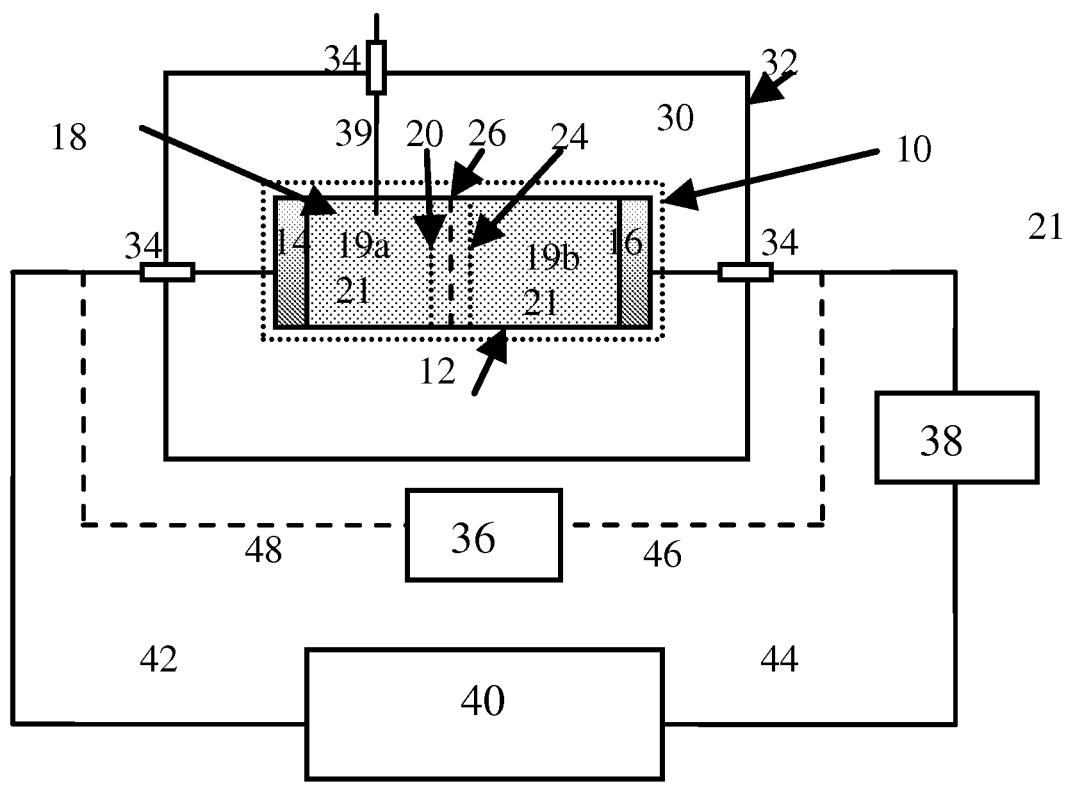
FIG. 1 shows one embodiment of a pH sensor of the present invention, for a situation in which the sample is separated from the pressurizing medium.

FIG. 1 provides an illustration of one embodiment of a sensor constructed in accordance with the present invention, for a situation where the sample fluid is separated from the pressurizing medium. As shown in FIG. 1, sensor 10 (shown demarcated by a dotted line) is constructed from a hollow body portion 12. Body portion 12 is constructed from a flexible material that is electrically insulating such as polymerized siloxane. A first electrode 14 is disposed at one end of body portion 12 so as to completely seal the end of the body portion. A second electrode 16 is disposed at the opposite end of the body portion 12 as the first electrode so as to completely seal the end of the body portion, thereby defining cavity 18. A first reverse osmosis membrane 20 and a second reverse osmosis membrane 24 are disposed within cavity 18 so as to divide the cavity 18 into two portions 19a and 19b, which contain sample fluid 21. A proton conducting membrane 26 is disposed between the first and second reverse osmosis membranes 20, 24. These components are arranged such that in travelling from the first electrode to the second electrode, a proton, or hydrogen ion would pass through the first reverse osmosis membrane, then the proton conducting membrane, and finally through the second reverse osmosis membrane before reaching the second electrode surface. The membranes may be so attached in a variety of ways, including the use of a frame of the same shape as the body portion 12, across which the said membranes are stretched to ensure a tight fit.

In the present embodiment, the sensor 10 is immersed within a pressurizing fluid 30, enclosed within a pressurizable vessel, 32.

The sensor 10 is shown in electrical communication with power source 40. A first wire 42 connects the power source to the first electrode, entering pressurizable vessel 32 via feedthrough attachment 34. A second wire 44 connects the power source to the second electrode, also entering pressurizable vessel 32 via feedthrough attachment 34. A current transducer, or ammeter 38 is connected in series with the circuit, residing either along wire 42 or wire 44 (as illustrated in FIG. 1). A voltage transducer, or voltmeter 36 is connected to wire 42 via wire 48 and to wire 44 via wire 46 in a manner to permit measurement of voltage across the sample. While it is possible in principle to locate both the ammeter 38 and voltmeter 36 within the pressurizing vessel 32, both these devices would need to withstand the pressure conditions under test. A preferred embodiment would locate both devices outside the pressure vessel 32 to avail of normally available instrumentation. A temperature sensor 39 may also be placed within the sample chamber to measure its temperature, with the sensor 38 being connected to an external data recording device (not shown), via a feedthrough attachment 34.

In use, a sensor of the present invention is filled with the sample fluid 21 in such a manner that the fluid fills cavity 18 (comprising portions 19a and 19b) without air inclusion. One preferred method for accomplishing this is to immerse the body portion 12 completely within a container filled with the sample fluid, eliminating air bubbles entirely, inserting the frame(s) assembled with membranes 20, 24 and 26 into it (described below), and finally, inserting electrodes 14 and 16 while so immersed. This results in a sensor with encapsulated sensor fluid 21 contained in cavities 19a and 19b as illustrated in FIG. 1. The frame with membranes 20, 24 and 26 may be assembled separately under water or other liquid, ensuring the elimination of air in the intrermembrane spaces. While the intermembrane space may be filled with the sample fluid or any other fluid as well, the use of water permits use of the sensor with a variety of aqueous sample fluids, which under pressure, would in any case, result in permeation of water into the intermembrane spaces. Other methods for sample loading may be used, for example solid samples may be cut to shapes that conform to chamber dimensions. The description of the method of loading above is not intended to restrict the manner of practice of this invention. Because the body portion is constructed of a flexible, electrically insulating material the fluid inside the sensor is constantly maintained at the same pressure as the fluid outside the sensor. At this time, the fluid sample's pH is measured.

After the sample is loaded, the power supply 40 is energized, to apply a voltage across electrodes 14 and 16. The voltage across the electrodes is measured by voltmeter 36 and the current flowing through the sample chamber by ammeter 38. The resulting data could be converted to an electrical conductivity, which is directly related to sample pH as discussed above, using standard methods for calculation of electrical conductivity (see for example, Crow, 1988. or Sastry, 2005) For systems of complex geometry, a cell constant may be determined. The sensor may be calibrated by determination of its response at atmospheric pressure against solutions of known pH. Under pressurized conditions, some corrections may be necessary, including a correction for sensor distortion under pressure, and viscosity changes in the sample medium. Sensor distortion under pressure may be corrected by determining cell constants under pressure and comparison to the cell constant under atmospheric conditions. Viscosity corrections involve the use of viscosity data under pressure, as for example, are available from the National Institute for Standards and Technology (NIST, 2007).

Figure 1A:
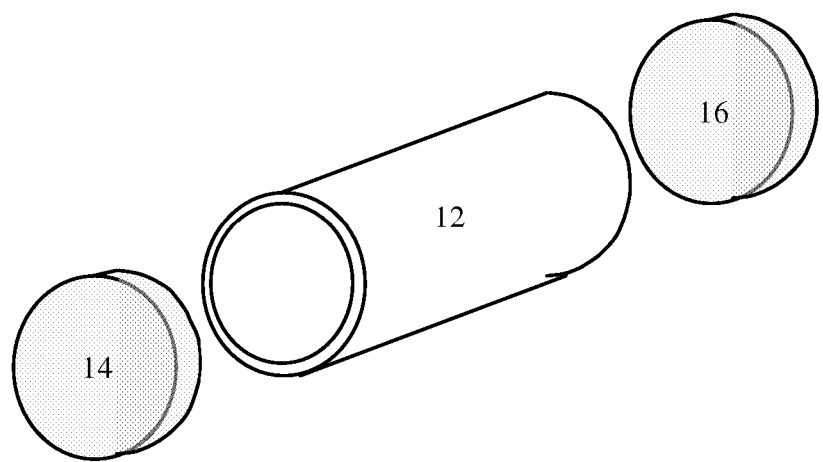
FIG. 1a provides an exploded view of one embodiment of the present invention.

A three-dimensional exploded view of a preferred embodiment is shown in FIG. 1a, where the electrodes 14 and 16 and body portion 12 are shown in exploded view. The electrodes 14 and 16 in this embodiment are circular in cross-section, with the body 12 forming a cylindrical tube. However, the electrodes and body may be of any other shape that mutually conform to one another and present a leak-proof seal.

Figure 2:
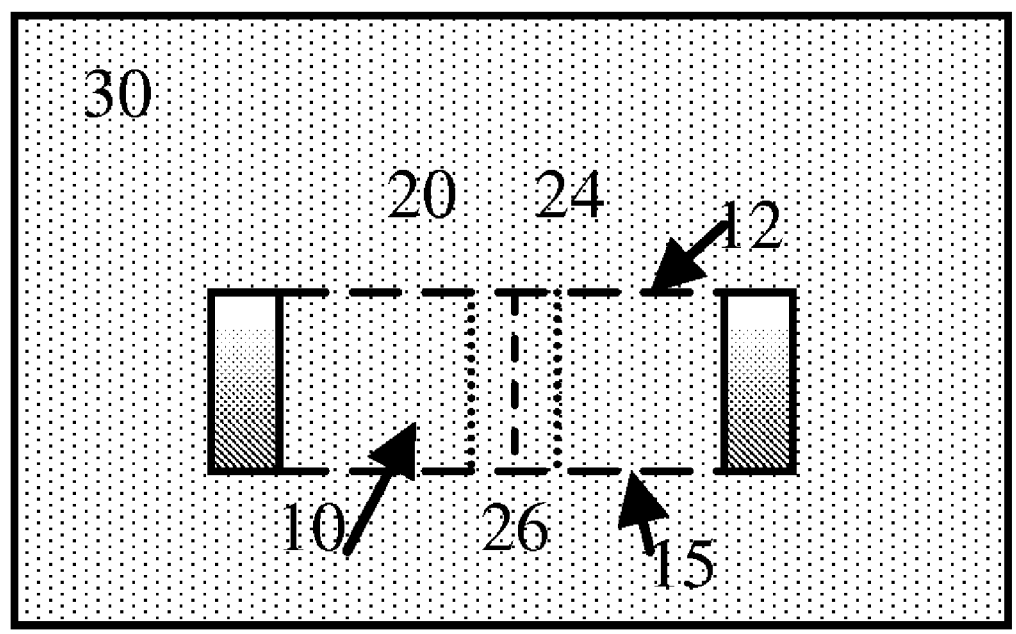
FIG. 2 shows another embodiment, where the sample and the pressurizing medium are comprised of the same material.

FIG. 2 represents another embodiment of this invention, for a situation where the sample fluid is the same as the pressurizing medium. The sensor 10 is shown (without the power supply and instrumentation wires for simplicity), with the same configuration as in FIG. 1, but with the body portion 12 consisting of perforations 15 to permit ingress of the pressurizing fluid 30 into the sample chamber. The operation of the sensor is as described previously.

While the invention has been described in connection with what is presently considered to be the most practical and preferred embodiments, it is to be understood that the invention is not to be limited to the disclosed embodiment(s), but on the contrary, is intended to cover various modifications and equivalent arrangements included within the spirit and scope of the appended claims, which are incorporated herein by reference.

The following references are incorporated herein by reference:

Crolet, J. L. and Bonis, M. R. (1983); pH measurements in aqueous $CO_2$ solutions under high pressure and temperature, Corrosion-NACE, 39 (2), 39-46.

Crolet, J. L. and Bonis, M. R. (1984); pH measurements under high pressures of $CO_2$ and $H_2S$. Materials Performance, May, 35-42.

Crow, D. R. 1988. Principles and Applications of Electrochemistry, Chapman and Hall, New York.

Cruanes, M. T., Drickamer, H. G. and Faulkner, L. R. (1992). Electrochemical measurements at high pressure: Solvation and thermodynamics of electron-transfer reactions. The Journal of Physical Chemistry, 96 (24), 9888-9892.

Disteche, A. (1959); pH measurements with a glass electrode withstanding 1500 kg/cm$^2$ hydrostatic pressure. The Review of Scientific Instruments, 30(6), 474-478.

El'yanov, B. S. (1975); Linear free energy relationship and some quantitative regularities of the effect of pressure on chemical reactions. Aust. J. Chem., 28, 933-943.

Hayert, M., Perrier-Cornet, J. and Gervais, P. (1999); A simple method for measuring the pH of acid solutions under high pressure. J. Phys. Chem. A, 103, 1785-1789.

Hitchens, T. K. and Bryant, R. G. (1998); Pressure dependence of weak acid ionization in deuterium oxide solutions. J. Phys. Chem. B, 102, 1002-1004.

NIST, 2007 Database http://webbook.nist.gov/cgi/.

DuPont., 2007 http://www.dupont.com/fuelcells/pdf/dfc101.pdf.

Kalinina, A. G. and Kryukov, P. A. (1976); Conductometric measurements at pressures from 1 to 7000 kg/cm$^2$. International Corrosion Conference Series, 158-163.

Kitamura, Y. and Itoh, T. (1987); Reaction volume of protonic ionization for buffering agents. Prediction of pressure dependence of pH and pOH. Journal of Solution Chemistry, 16 (9), 715-725.

Sastry, S. K. 2005. Electrical Conductivity of Foods. Chapter 10 in: Engineering Properties of Foods, M. A. Rao, S. S. H. Rizvi and A. K. Datta, Eds. CRC Press, Boca Raton, Fla.

Stippl, V. M., Delgado, A. and Becker T. M. (2002); Optical method for the in-situ measurement of the pH-value during high pressure treatment of foods. High Pressure Research, 22, 757-761.

What is claimed is:

1. A sensor for measuring the pH of a solution, said sensor comprising:
   a tubular body portion constructed from a flexible electrically-insulating material, said tubular body portion having an interior passage;
   a first reverse osmosis membrane disposed in said interior passage;
   a second reverse osmosis membrane disposed in said interior passage;
   a proton conducting membrane disposed between said first reverse osmosis membrane and said second reverse osmosis membrane in said interior passage;
   a first electrode disposed at one end of said tubular body portion; and
   a second electrode disposed at an opposite end of said.

2. The sensor for measuring pH of a solution according to claim 1 additionally comprising a power supply in electrical communication with said first electrode and said second electrode.

3. The sensor for measuring pH of a solution according to claim 1 wherein said electrically-insulating material is flexible.

4. The sensor for measuring pH of a solution according to claim 3 wherein said electrically-insulating material is flexible in the pressure range of from about 1 MPa to about 1000 MPa.

5. The sensor for measuring pH of a solution according to claim 1 wherein said proton conducting membrane is a Nafion membrane.

6. The sensor for measuring pH of a solution according to claim 1 wherein said electrically-insulating material is a polymerized siloxane.

7. The sensor for measuring pH of a solution according to claim 1 wherein said sensor is operational in the pressure range of from about 1 MPa to about 1000 MPa.

8. The sensor for measuring the pH of a solution according to claim 1 wherein said first electrode comprises a material selected from the group consisting of: gold, platinum, titanium, boron-doped diamond, and graphite.

9. The sensor for measuring the pH of a solution according to claim 1 wherein said second electrode comprises a material selected from the group consisting of: gold, platinum, titanium, boron-doped diamond, and graphite.

10. The sensor for measuring the pH of a solution according to claim 1 wherein said first reverse osmosis membrane is a thin film membrane.

11. The sensor for measuring the pH of a solution according to claim 1 wherein said second reverse osmosis membrane is a thin film membrane.

* * * * *